(12) United States Patent
Nagano et al.

(10) Patent No.: US 6,228,490 B1
(45) Date of Patent: May 8, 2001

(54) SPLITTABLE CONJUGATED FIBER AND NONWOVEN FABRIC USING THE SAME, AND ABSORBENT ARTICLE

(75) Inventors: Koki Nagano; Toshihiko Tsutsui, both of Shiga (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/398,728

(22) Filed: Sep. 17, 1999

(30) Foreign Application Priority Data

Sep. 21, 1998 (JP) .................................................. 10-266945

(51) Int. Cl.[7] ........................................................ D01F 8/00
(52) U.S. Cl. ........................ 428/370; 428/373; 428/374; 428/372
(58) Field of Search ..................................... 428/370, 373, 428/374, 372

(56) References Cited

U.S. PATENT DOCUMENTS 5,683,814 * 11/1997 Kakita et al. ........................ 428/397
5,759,926 * 6/1998 Pike et al. ............................. 428/374
5,783,503 * 7/1998 Gillespie et al. ..................... 428/374
6,004,673 * 12/1999 Nishijima .............................. 428/373
6,080,471 * 6/2000 Shigematsu et al. ............. 428/311.11

FOREIGN PATENT DOCUMENTS 3-137222   6/1991   (JP) .
5-321018   12/1993  (JP) .

* cited by examiner

Primary Examiner—N. Edwards
(74) Attorney, Agent, or Firm—Merchant & Gould P.C.

(57) ABSTRACT

A polyolefin-based splittable conjugated fiber which contains a peroxide and has a melt flow rate of at least 30 g/10 min, and a nonwoven fabric comprising split fibers obtained by splitting the splittable conjugated fiber, and an absorbent article using the nonwoven fabric in a part thereof. The polyolefin-based splittable conjugated fiber has good spinnability and good stretchability, and is easy to split. This invention further provides a nonwoven fabric that is soft and uniform and has a good formation, and an absorbent article using such a nonwoven fabric in a part thereof, by solving the difficulty in splitting for a polyolefin-based splittable conjugated fiber, which has been its conventional problem.

6 Claims, 6 Drawing Sheets

SPLITTABLE CONJUGATED FIBER AND NONWOVEN FABRIC USING THE SAME, AND ABSORBENT ARTICLE

FIELD OF THE INVENTION

The present invention relates to a polyolefin-based splittable conjugated fiber having excellent splittability, and to a nonwoven fabric and an absorbent article using the same. More particularly, the present invention relates to a polyolefin-based splittable conjugated fiber that can display excellent characteristics with extra fine fiber generated by splitting, and which can be used suitably in battery separators, wipers, filters, and the like, and a nonwoven fabric using the same, and to an absorbent article such as a disposable diaper, sanitary napkin, menstrual sheet, incontinence pad, nursing pad, or the like, in which such a nonwoven fabric is partially used.

BACKGROUND OF THE INVENTION

Traditionally, splittable conjugated fiber has been used in various applications, because it forms extra fine fiber by splitting treatment.

As a conventional olefin-based splittable conjugated fiber, Publication of Examined Japanese Patent Application (Tokko) No. HEI 3-137222 (JP 3-137222 B) discloses one in which the hardness of a polymer is determined, and Publication of Unexamined Japanese Patent Application (Tokkai) No. HEI 5-321018 (JP 5-321018 A) discloses one in which a polypropylene resin is combined with a polyethylene resin blended with a polypropylene resin.

In the invention disclosed in the above-mentioned Publication of Japanese Examined Patent Application (Tokko) No. HEI 3-137222, it is described that the fiber can be split easily when the polymer itself has a hardness of not less than a certain value. However, there was a problem in that, when the polymer has a high hardness, its spinnability as well as its stretchability become poor, so that the fineness of the fiber before being split becomes large. Moreover, in the invention disclosed in the above-mentioned Publication of Unexamined Japanese Patent Application (Tokkai) No. HEI 5-321018, a polypropylene resin (a) is used as one component of the splittable conjugated fiber, and a blended resin (b) in which a polyethylene resin is blended with a polypropylene resin is used as the other component. However, when a polyethylene resin is blended with a polypropylene resin, it has an increased compatibility with the polypropylene resin (a), so that these components become difficult to split. Thus, it is necessary to increase the physical impact to split the splittable conjugated fiber. However, when the physical impact is increased, unevenness is generated in the density of the fiber existing in the obtained nonwoven fabric, so that non-uniformity is generated, and formation is deteriorated. Moreover, production of a nonwoven fabric having a low basis weight, for example, a nonwoven fabric for sanitary materials, becomes difficult. Thus, it was not satisfactory at all.

SUMMARY OF THE INVENTION

The present invention has an object to provide an olefin-based splittable conjugated fiber that can improve these drawbacks, and a nonwoven fabric using the same, and an absorbent article.

That is, it is an object of the present invention to provide an olefin-based splittable conjugated fiber that has good spinnability and good stretchability, and is easy to split.

It is another object of the present invention to provide a nonwoven fabric that is soft and uniform and has a good formation by solving the difficulty in splitting, which has been a conventional problem for a polyolefin-based splittable conjugated fiber, and to provide an absorbent article in which such a nonwoven fabric is partially used.

The present invention is characterized as follows:

(1) A polyolefin-based splittable conjugated fiber which contains a peroxide and has a MFR of at least 30 g/10 min.

(2) The polyolefin-based splittable conjugated fiber according to the item (1), which comprises a polypropylene resin and a polyethylene resin.

(3) The polyolefin-based splittable conjugated fiber according to the item (1), wherein the peroxide is dialkylperoxide.

(4) The polyolefin-based splittable conjugated fiber according to the item (1), wherein the content of the peroxide is from 0.005 to 0.3 wt. % based on the total weight of the polyolefin-based splittable conjugated fiber.

(5) The polyolefin-based splittable conjugated fiber according to the item (1), which has a modified cross section (non-circular cross section).

(6) A nonwoven fabric, comprising split fibers obtained by splitting the splittable conjugated fiber according to the item (1).

(7) An absorbent article using the nonwoven fabric according to the item (6) in a part thereof.

DETAILED DESCRIPTION OF THE INVENTION

Figure 1:
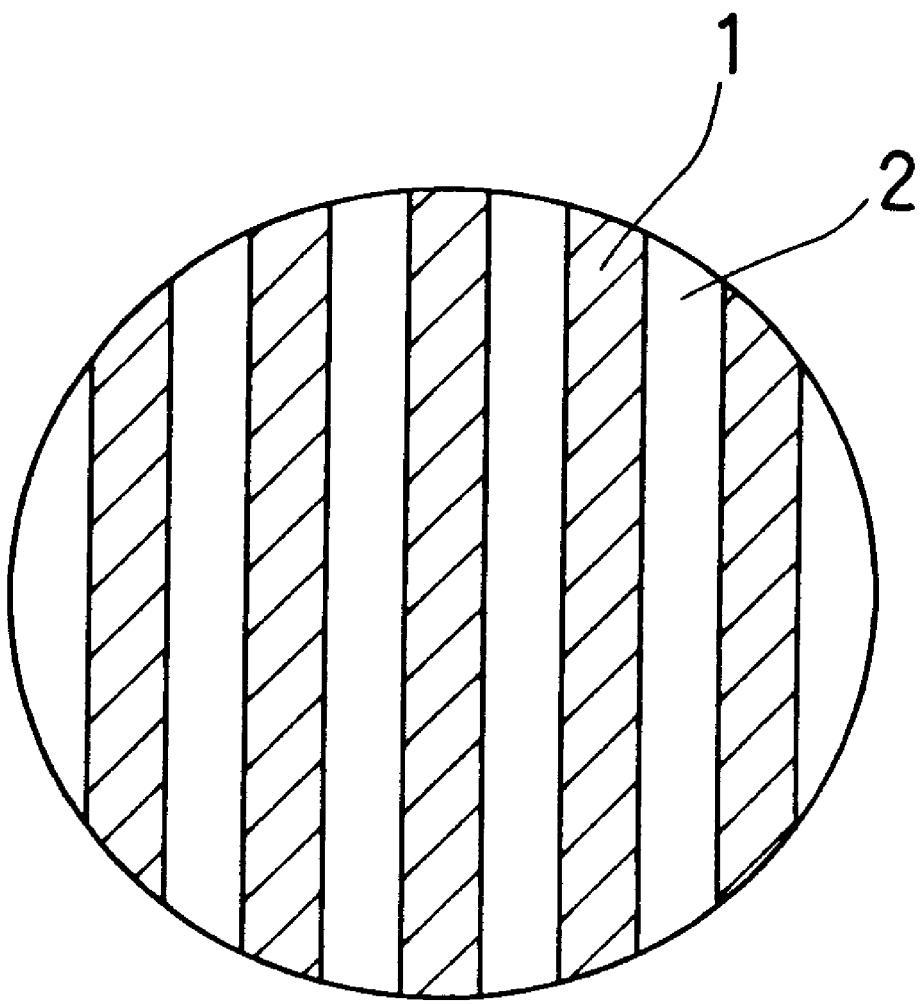
FIG. 1 is a cross-sectional view of a splittable conjugated fiber of the present invention.

The present invention is further described in detail below.

The polyolefin-based splittable conjugated fiber as in the present invention is a fiber that contains a peroxide mentioned below and has a MFR (melt flow rate) of at least 30 g/10 min.

As the splittable conjugated fiber has a better stretchability, i.e. a larger stretching ratio, its split ratio may be increased. In order that the splittable conjugated fiber has a good stretchability, it is necessary to have a MFR of at least 30 g/10 min. Moreover, although there is particularly no upper limit for the MFR, it is preferably not more than 200 g/10 min in view of spinnability. That is, because melt-spinning tends to be hard to perform when the MFR is too high, it is preferable that the MFR of the splittable conjugated fiber is not more than 200 g/10 min.

The polyolefin resins used for the components of the splittable conjugated fiber of the present invention include a polypropylene resin, a polyethylene resin, and further, polyolefin copolymers that are crystalline copolymers of α-olefins having from 2 to 8 carbon atoms such as ethylene, propylene, butene-1, hexene-1, octene-1, 4-methylpentene-1, and the like, e.g. ethylene/propylene copolymer and ethylene/propylene/1-butene terpolymer.

The increasing characteristic of the MFR during spinning is varied among the polyolefin resins depending on the types of the resins. For example, resins having a main component containing many tertiary carbon atoms such as a propylene polymer are decomposition-type, in which polymer molecules are decomposed to increase the MFR considerably during spinning. On the other hand, resins having a main component containing few tertiary carbon atoms such as an ethylene polymer are crosslinking-type, in which the MFR does not increase significantly during spinning. Accordingly, in the following, a resin using polypropylene as a main component will be described as a typical example of the decomposition-type, and a resin using polyethylene as a main component will be described as a typical example of the crosslinking-type.

The polypropylene resin used in the present invention is a fiber-forming crystalline polypropylene, and the MFR of the polymer before spinning may be either high or low. However, it is important that during spinning the MFR of the polypropylene resin is at a level that shows good spinnability and permits easy stretching as well as easy splitting. Usually, the MFR of the polypropylene resin changes while it is formed from a raw material polymer into fiber. The MFR of the polypropylene resin before stretching is subject to heat history and shearing as it is passed through an extruder, discharged from a spinning nozzle, and is taken up. Accordingly, the polypropylene molecules are cut, so that the MFR of the fiber becomes higher than that of the raw material polymer.

As a polypropylene resin having good spinnability and good stretchability, it is preferable to use a polymer having a high MFR during spinning. As such a polypropylene resin, one having a high MFR as a raw material polymer, or one achieving a high MFR during spinning by any means even though it has a low MFR as a raw material polymer, can be used. According to the present invention, a peroxide is contained in the raw material polymer to increase the MFR during spinning. Because the spinning is carried out at a high temperature, the peroxide added to the raw material polymer at this time acts to cut the main chain of the polypropylene molecule, so that the polypropylene resin has a high MFR during spinning.

By the way, the non-oriented fiber using a polymer having a high MFR as a raw material, and the non-oriented fiber in which the MFR after spinning is increased by the use of the peroxide show different behaviors during stretching. That is, the maximum stretching ratio of the non-oriented fiber in which the MFR is increased after spinning by the use of the peroxide is higher than that of the non-oriented fiber having a high MFR as a raw material polymer. It is considered that this occurs because they have different molecular-weight distributions, even though they have the same MFR. The non-oriented fiber of a raw material polymer having a high MFR has a wide molecular-weight distribution, so that it is difficult to stretch. On the other hand, in the non-oriented fiber in which the MFR is increased after spinning by the use of the peroxide, molecules with high molecular-weights are cut to decrease the molecular-weight distribution, so that it is easy to stretch.

The non-oriented fiber of the polypropylene resin in which the MFR during stretching is increased by using a peroxide in the raw material polymer with a low MFR has a good stretchability, and its molecular orientation is promoted considerably by the stretching. Thus, a large strain can be developed between the polypropylene resin and the polyethylene resin it is to be split from. That is, the polypropylene component and the polyethylene component in the non-oriented conjugated fiber penetrate with each other at their boundary. It is assumed that orientation of each component is promoted by the stretching, and as a result, the condition in which the polypropylene component and the polyethylene component penetrate with each other at their boundary is dissipated, and their boundary becomes approximately smooth so that the fiber becomes easy to split. Accordingly, with the strain thus generated, the splittable conjugated fiber comprising the polypropylene resin and the polyethylene resin, which is a combination considered difficult to split due to its inherent good compatibility, that is, a splittable conjugated fiber comprising different polyolefin resins, can be split easily.

On the other hand, unlike the polypropylene resin, which is the decomposition-type to heat, the polyethylene resin is not the decomposition-type to heat, but is the crosslinking-type. Thus, there is almost no difference between the MFR of the polyethylene resin as a raw material and the MFR of the non-oriented fiber discharged from a spinning nozzle through an extruder. It is considered that, this is because the polyethylene resin is crosslinked by heat in a degree corresponding to the degree of molecules that are cut by shearing with the extruder. Thus, when a polyethylene resin is used in a splittable conjugated fiber, it is desirable to use one having a high MFR at the stage of a raw material polymer, which is considered to have somewhat good spinnability as well as good stretchability.

However, in the case of a polyethylene resin, when a peroxide is added, the molecule of the polyethylene also is cut by the peroxide. Thus, its spinnability is improved, although it is in a less degree than in the case of a polypropylene resin. Therefore, the effect of improving the stretchability, which influences the splittability of the splittable conjugated fiber, is achieved by the addition of the peroxide, so that the splittability of the splittable conjugated fiber is improved.

When the polypropylene resin as a raw material polymer itself has a high MFR (e.g. from 30 to 40 g/10 min), its spinnability and stretchability are not at poor levels without adding a peroxide. However, in this case, the non-oriented fiber of the splittable conjugated fiber obtained has a wide molecular-weight distribution, so that its stretchability is not sufficient. When the polypropylene resin as a raw material polymer itself has a low MFR (e.g. from 5 to 10 g/10 min), by containing a necessary amount of a peroxide, a splittable conjugated fiber that has good spinnability and good stretchability and is easy to split can be obtained.

Because many peroxides are expensive, and also so as not to cause problems in spinnability such as filament breakage as a foreign matter, it is preferable that the content of the peroxide is from 0.005 to 0.3 wt. % based on the total weight of the splittable conjugated fiber. It is herein understood that the total weight of the splittable conjugated fiber refers to the total weight of the splittable conjugated fiber including the weight of the peroxide contained. The peroxide may be contained in at least any one of the plurality of components of polyolefin resins constituting the splittable conjugated fiber, but also may be contained in all the resin components. Although not particularly limiting, when the peroxide is added to only any one of the resin components, it is preferably added to the resin component having a larger amount of tertiary carbon atoms as mentioned above, because it provides better efficiency for increasing the MFR in the entire conjugated fiber.

Table 1 in the Examples of the present invention shows the content of a peroxide for each of the polyolefin resin components constituting the splittable conjugated fiber. These values can be converted into the contents based on the total weight of the splittable conjugated fiber by simple calculations. When the content of the peroxide based on the total weight of the splittable conjugated fiber is determined as X wt. %, the content of the peroxide added to the first polyolefin resin component is determined as $A_1$ wt. %, the content of the peroxide added to the second polyolefin resin component is determined as $A_2$ wt. %, . . . and the content of the peroxide added to the polyolefin resin component of the n-th order is determined as $A_n$ wt. %; and the composite ratio of the first polyolefin resin component is determined as $B_1$ wt. %, the composite ratio of the second polyolefin resin component is determined as $B_2$ wt. %, . . . and the composite ratio of the polyolefin resin component of the n-th order is determined as $B_n$ wt. %, it is expressed by the equation: $X=(A_1 \times B_1 + A_2 \times B_2 + \ldots + A_n \times B_n)/100$.

Molecular-weight reducing agents for polyolefin resins to increase the MFR of the polymer include azo compounds, peroxides, and the like. In the present invention, it is necessary to use a peroxide in view of the small dissociation energy of a peroxidation bond.

Examples of the peroxide include hydroperoxide, dialkylperoxide, diacylperoxide, peroxyester, ketone peroxide, and the like. Although not particularly limiting, one having a molecular weight of 50 to 400 is preferably used as the hydroperoxide; one having a molecular weight of 62 to 1100 is preferably used as the dialkylperoxide; one having a molecular weight of 118 to 1200 is preferably used as the diacylperoxide; one having a molecular weight of 90 to 800 is preferably used as the peroxyester; and one having a molecular weight of 90 to 2000 is preferably used as the ketone peroxide. Among these, it is particularly preferable to use a dialkylperoxide, which does not contain a polar group and is chemically stable.

Examples of the dialkylperoxide include ditertiarybutylperoxide, dicumylperoxide, 2,5-dimethyl-2,5-di(tertiarybutylperoxy)hexane, 1,3-bis(tertiarybutylperoxyisopropyl)benzene, and the like. Among these, 2,5-dimethyl-2,5-di(tertiarybutylperoxy)hexane and 1,3-bis(tertiarybutylperoxyisopropyl)benzene, in which the alkyl group is a tertiary alkyl group, are particularly preferable.

Although not particularly limiting, it is preferable that the length of the above-mentioned splittable conjugated fiber is from 3 to 128 mm. More preferably, it is from 3 to 76 mm, still more preferably, from 5 to 64 mm. Generally, when the length of the fiber is considerably shorter than 3 mm, there is a tendency that a physical impact is hard to apply, so that the splittable conjugated fiber becomes difficult to split. Also, when the length of the fiber exceeds 128 mm considerably, there is a tendency that the fiber cannot be formed into a web uniformly, so that a web having a uniform formation cannot be produced. Thus, when a splittable conjugated fiber having a length of 3 to 128 mm is used, good splittability is exhibited, and a web having a uniform formation can be produced.

The thickness of the splittable conjugated fiber is preferably from 1 to 100 dtex, more preferably from 1.5 to 35 dtex, still more preferably from 1.5 to 20 dtex. Moreover, dtex is the weight of a fiber with a length of 10,000 m. When the thickness of the fiber is smaller than 1 dtex considerably, there is a tendency that its passability through a carding apparatus deteriorates, and its productivity is decreased. On the other hand, when the thickness of the fiber exceeds 100 dtex considerably, there is a tendency that the entangling force of the fiber increases. Thus, the dispersibility of the fiber is lowered, and a web having a uniform formation is difficult to produce. When the thickness of the splittable conjugated fiber is in the range of 1 to 100 dtex, it has a good passability through a carding apparatus, so that productivity of a web also is good. Moreover, the fiber has a good dispersibility, and a web with a uniform formation without unevenness can be produced.

When a web is produced by a wet process, considering the dispersibility of fiber in water, it is preferable that crimps are not provided to the fiber. Also, when a web is produced by a dry process, considering the carding passability, it is preferable to provide crimps to the fiber, choosing the shape and number of the crimps as appropriate depending on the fineness of the fiber. When the fineness is 1 dtex, the number of the crimps is preferably about 10 to 20 crimps per 25 mm. When the fineness is 100 dtex, the number of the crimps is preferably about 4 to 9 crimps per 25 mm. That is, the number of the crimps may be small as the fineness of the fiber becomes greater.

Examples of the form of the conjugated fiber include side-by-side type, multi-layer type with at least three layers, hollow multi-layer type, multi-layer type with modified cross section (multi-layer type with non-circular cross section), radial type, hollow radial type, and the like. Moreover, any form may be employed as long as one polyolefin resin component does not surround the other polyolefin resin component completely. That is, any form may be employed as long as it does not have a configuration in which one polyolefin resin component surrounds the other polyolefin resin component completely in a cross section of the fiber, as in a core/sheath type conjugated fiber.

Figure 2:
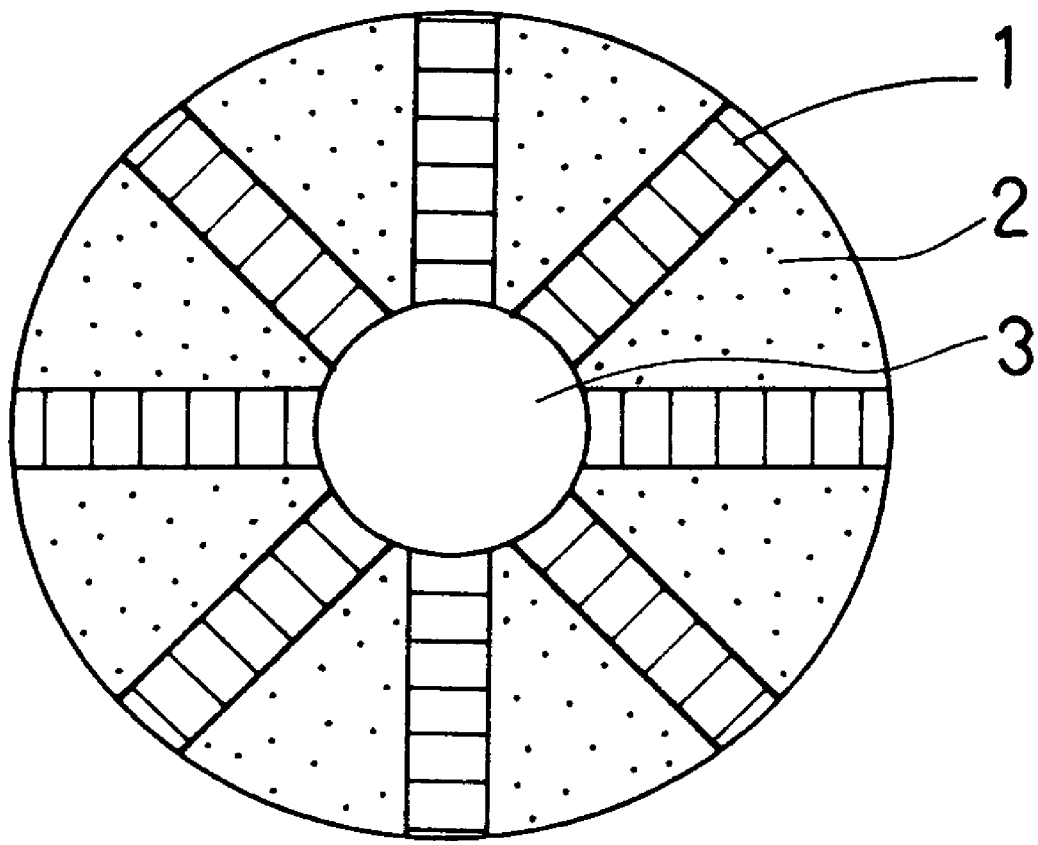
FIG. 2 is a cross-sectional view of a hollow splittable conjugated fiber of the present invention.

Specifically, using a polypropylene resin as the first polyolefin resin component and a polyethylene resin as the second polyolefin resin component, typical forms of conjugated fiber will be described referring to the cross-sectional views in a plane perpendicular to the length direction of the fiber, for example, as follows:

That is, typical examples of the forms of the splittable conjugated fiber include a form in which a polypropylene resin and a polyethylene resin are arranged in a multi-layer side-by-side type comprising two components (FIG. 1); a form in which a polypropylene resin and a polyethylene resin are arranged in a hollow and radial type comprising two components (FIG. 2); a form comprising a portion of polypropylene resin having a petaloid shape (radial shape) and a portion of polyethylene resin having a shape complementing the radial portion (FIG. 3); or the opposite form thereof (FIG. 4); and the like. In the drawings, numeral 1 indicates a high melting point polyolefin resin component (polypropylene is herein used), numeral 2 indicates a low melting point polyolefin resin component (polyethylene is herein used), and numeral 3 indicates a hollow portion. Moreover, when the splittable conjugated fiber comprises a polypropylene resin and a polyethylene resin, the resin having a higher melting point, i.e., in this case the polypropylene resin, becomes the high melting point component, and the resin having a lower melting point, i.e., in this case the polyethylene resin, becomes the low melting point component. Moreover, of course, combinations of polyolefin resins other than that of a polypropylene resin and a polyethylene resin also may be employed.

Figure 4:
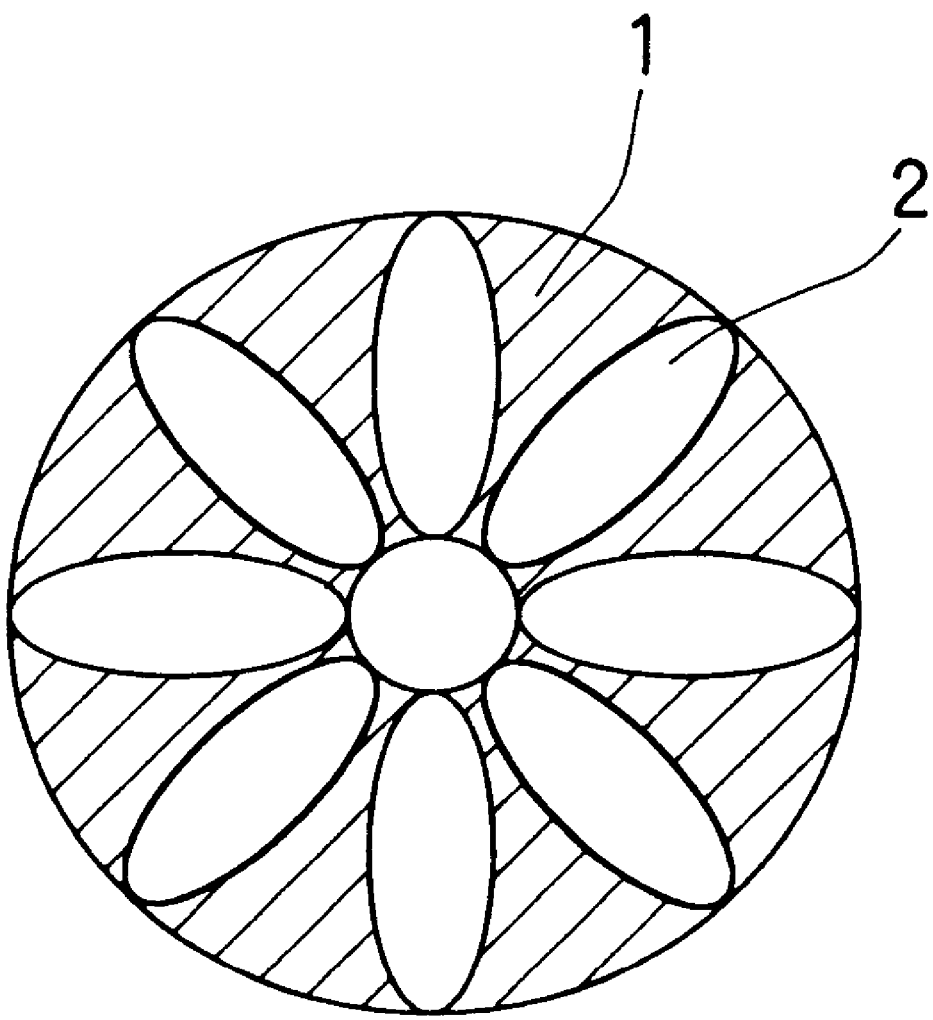
FIG. 4 is a cross-sectional view of a splittable conjugated fiber of the present invention.
Figure 5:
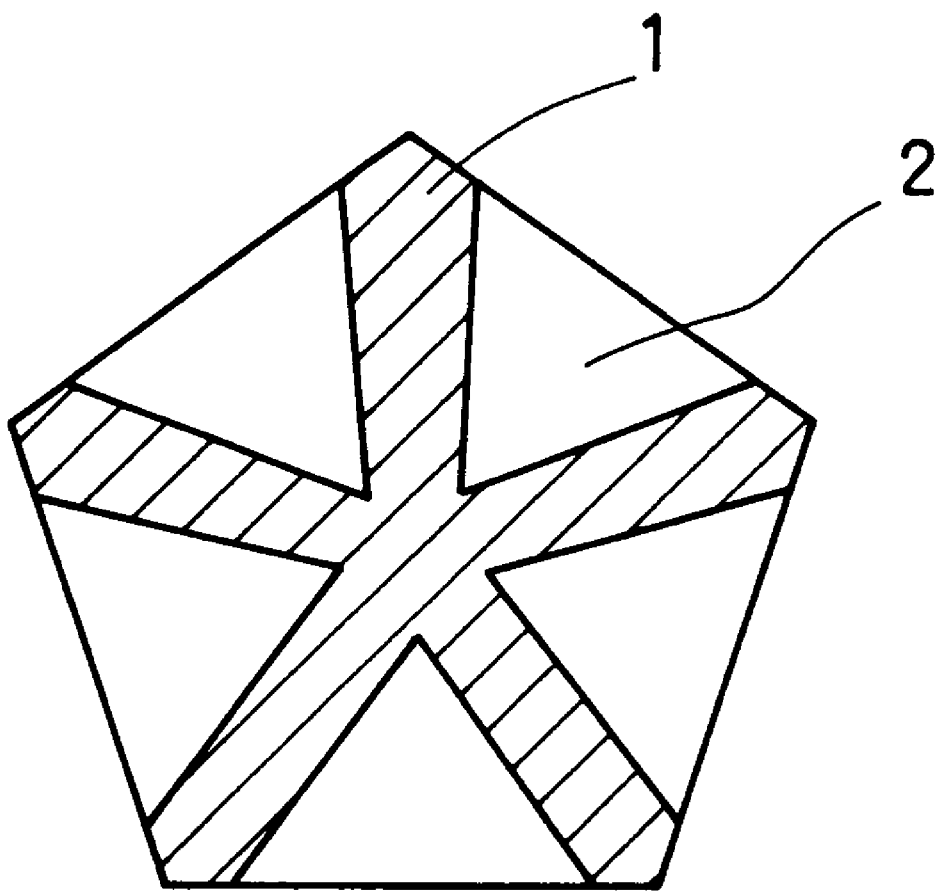
FIG. 5 is a cross-sectional view of a splittable conjugated fiber having a modified cross section (non-circular cross section) of the present invention.

Moreover, considering that the splittable conjugated fiber is split by receiving a physical impact, it is desirable that the splittable conjugated fiber has a modified cross section (non-circular cross section), which is suitable to receive a physical impact. Examples of the modified cross section are ellipse, triangle, quadrangle, pentagon (FIG. 5), star-shape (FIG. 6), and the like. Any shape may be employed as long as a physical impact can be applied easily and an excellent result can be obtained in the easiness of splitting, which is an object of the present invention. Also, the arrangement of each resin component and the shape of the cross section are not particularly limited to those shown in the drawings. Moreover, numerals 1 and 2 in these drawings have the same meanings as in case of the above-mentioned FIGS. 1 to 4.

In the splittable conjugated fiber of the present invention, it is preferable that the composite ratio of the first polyolefin resin component and the second polyolefin resin component is in the range of 10:90 to 90:10% by weight, more preferably from 30:70 to 70:30% by weight. By having a composite ratio in this range, splitting is made easy, and moreover, a conjugated fiber having a cross section with a configuration that allows each resin component to split easily so that one resin component does not surround the other resin component completely, e.g. as in a core/sheath type conjugated fiber, can be obtained easily. Furthermore, the unit of the composite ratio in the following description also is percentage by weight.

The splittable conjugated fiber of the present invention can be produced, for example, by the steps as follows: A first polyolefin resin and a second polyolefin resin containing a peroxide are melted, and are discharged from, for example, a composite spinneret having 500 to 1000 holes. At this time, a portion directly under the spinneret is cooled by air, and a non-oriented fiber is obtained. By taking up the fiber at a discharge rate of 100 to 200 g/min and a take-up speed of 40 to 1300 m/min, a non-oriented fiber with a thickness of 3 to 400 dtex is produced. The non-oriented fiber is stretched between rolls heated at a temperature in the range between 60° C., and the temperature lower by 15° C. than the melting point of the resin with the lowest melting point among the resin components used (for example, in the case of the combination of a polypropylene resin and a polyethylene resin, between 60° C. and 120° C.). By stretching with a ratio of the rotating speeds of the first and the second rolls set in the range between 1:5 and 1:7, an oriented fiber with a thickness of 1 to 100 dtex is produced. After applying a finishing agent to the oriented fiber with a touch roll, the fiber is passed through a crimp-finishing machine of box type, and a tow having crimps is produced. The number of the crimps is preferably from 0 to 25 crimps per 25 mm. Because the tow contains about 10 wt. % of moisture, it is dried with a drier at a temperature in the range between 60° C. and the temperature lower by 15° C. than the melting point of the resin having the lowest melting point among the resin components used (for example, in the case of the combination of a polypropylene resin and a polyethylene resin, between 60° C. and 120° C.). The dried tow is cut into fibers with a certain length, preferably in the range of 3 to 128 mm, with a push cutter.

Because the splittable conjugated fiber thus produced has an increased MFR, the rigidity of the fiber is decreased. Thus, it is preferable to blend it with other fiber having a large rigidity to improve its carding passability. Examples of the fiber to be blended with include polypropylene fiber, polyester fiber, polyester hollow fiber, and the like.

The nonwoven fabric of the present invention can be produced by using a staple fiber of the splittable conjugated fiber obtained above, which preferably has a length of 3 to 128 mm, and using a water-jet apparatus as follows:

When the length of the fiber is from 3 to 25 mm, the fiber is dispersed uniformly by a wet process, then strained, and processed by water jet, so that the fiber is split and simultaneously entangled to form a nonwoven fabric. Alternatively, the fiber is split with a beater, then strained and heat treated, so that the polyolefin resin as a low melting point component is melted and bonded to form a nonwoven fabric. In this case, the water-jet process is not required.

When the length of the conjugated fiber exceeds 25 mm, it is preferable that the web is produced with a carding apparatus and is processed by water jet, so that the conjugated fiber is split and simultaneously entangled to form a nonwoven fabric.

The splittable conjugated fiber of the present invention can be split by the above-mentioned splitting treatment in a high split ratio of at least 80%. Thus, improvement in feeling and increase in strength of the nonwoven fabric, which are the effects of extra thin fiber generated by the splitting treatment, can be displayed sufficiently. Moreover, it is assumed that a nonwoven fabric having a high strength can be obtained because the number of the fibers constituting the nonwoven fabric is increased by the splitting treatment, and thus the number of entanglement among the fibers is increased.

The nonwoven fabric of the present invention comprising the extra thin fiber obtained by splitting the splittable conjugated fiber is very soft, and is particularly suitable for uses touching the body, for example, disposable diapers, sanitary napkins, and the like.

The nonwoven fabric using the olefin-based splittable conjugated fiber of the present invention can be used suitably in an absorbent article. For example, in the case of a disposable diaper, it may be used suitably for a top surface nonwoven fabric (top sheet), a second sheet, or a back surface sheet (back sheet), etc. Particularly, because the nonwoven fabric comprises the splittable conjugated fiber comprises extra thin fiber, it is suitable as a top surface nonwoven fabric of an absorbent article that requires softness.

Furthermore, the nonwoven fabric using the splittable conjugated fiber of the present invention may be used as a wiping cloth or the like for furniture, automobiles, etc., with various types of lubricants adhered.

Furthermore, the nonwoven fabric using the splittable conjugated fiber may be formed into a filter medium by after-processing, for example, folding in pleats, winding into a cylindrical shape, or winding it while heating to form thermally melt-bonded cylindrical layers.

The present invention will be further described in detail below with reference to the following non-limiting examples.

The definitions and measuring methods for the values of the properties of polymers etc. in the examples are as follows:

(1) Spinnability

Spinnability was determined by the number of times of filament breakage during spinning of 100 kg.

◯: No filament breakage occurred.

Δ: Filament breakage occurred 1 to 3 times.

×: Filament breakage occurred at least 4 times.

(2) Stretchability

Stretchability was determined by the maximum stretching ratio when the total fineness of the non-oriented fiber was 100,000 dtex, and the speed of the oriented fiber when passed through the final stretching roll was 60 m/min.

◯: at least 7 fold

Δ: at least 6 fold but less than 7 fold

×: less than 6 fold

Moreover, explaining an example of a stretching ratio of 6 fold in the above, because the speed of the oriented fiber when passed through the final stretching roll is 60 m/min, the speed of the fiber when passed through the first stretching roll on the side of supplying the non-oriented fiber becomes 10 m/min.

(3) Resin MFR and Fiber MFR

Measurements were carried out in accordance with the condition 14 of JIS K7210 (Test Temperature: 230° C., Test Load: 2.16 kgf).

(4) Split Ratio

A sample was embedded in a wax, and cut approximately perpendicular to the fiber axis with a microtome so as to obtain a test piece. The test piece was observed with a microscope, and using the cross-sectional image obtained, a total cross-sectional area (A) of the extra thin fibers generated by splitting and a total cross-sectional area (B) of the unsplit splittable conjugated fiber were measured by image processing, and calculation was made according to the following equation $$\text{Split Ratio } (\%) = \{A/(A+B)\} \times 100.$$

Moreover, samples were taken from ten places in a material to be measured, and the average value for the ten samples was determined as the split ratio. The image processing was performed using an image processing apparatus manufactured by Nippon Avionics Co., Ltd.

(5) Strength of Nonwoven Fabric

The rupture strength and the strength at 10% extension of the nonwoven fabrics in the examples and comparative examples were measured according to the conditions below.

Conditions for Measuring the Strength of Nonwoven Fabric

Machine Used: Shimadzu AUTOGRAPH AG500 (manufactured by Shimadzu Corporation)

Size of Sample: 5 cm×15 cm

MD strength is the strength in the machine direction of a nonwoven fabric.

CD strength is the strength in the direction perpendicular to the machine direction (cross direction) of a nonwoven fabric.

Space between Chucks: 10 cm speed of Stretching: 200 mm/min

Number of Test Pieces: 10

The rupture strength is the strength when a nonwoven fabric is ruptured.

The strength at 10% extension is the strength when a nonwoven fabric is extended by 10%.

All values are the average of 10 test pieces.

(6) Formation of Nonwoven Fabric

Uniformity of fiber in a nonwoven fabric (1 m square) after splitting was evaluated by ten panelists with their naked eyes as follows:

◯: At least 7 people felt that it is uniform.

Δ: At least 4 but not more than 7 people felt that it is uniform.

×: Not more than 3 people felt that it is uniform.

EXAMPLE 1

Figure 3:
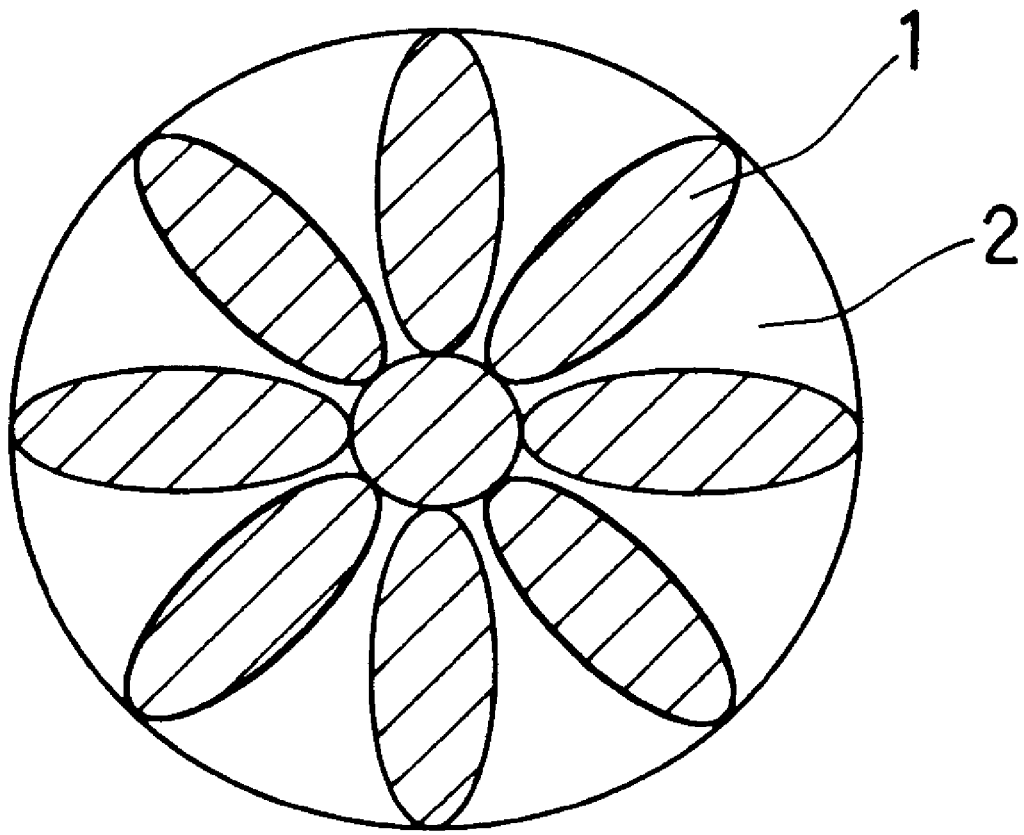
FIG. 3 is a cross-sectional view of a splittable conjugated fiber of the present invention.

Using PP1 in Table 1 as a raw material polypropylene resin (hereinafter abbreviated as PP), and PE1 in Table 1 as a raw material polyethylene resin (hereinafter abbreviated as PE), composite spinning was carried out at 300° C. to obtain a non-oriented fiber having a thickness of 8 dtex and having a cross-sectional shape as shown in FIG. 3. In FIG. 3, numeral 1 indicates a high melting point polyolefin resin component (in this case PP), and numeral 2 indicates a low melting point polyolefin resin component (in this case PE). Unless particularly stated otherwise, in the following examples and comparative examples, numerals 1 and 2 indicate a high melting point polyolefin resin component and a low melting point polyolefin resin component, respectively.

After stretching the thus obtained non-oriented fiber by a stretching ratio of 6 fold, it was crimped and cut with a push cutter, so that a splittable conjugated fiber having a fineness based on corrected weight of 1.6 dtex, a length of 45 mm, and 13 crimps per 25 mm was obtained.

Table 2 shows PP/PE ratio (wt. %), rupture strength, rupture elongation, fiber MFR, cross-sectional shape, spinnability, and stretchability. Moreover, the fineness based on corrected weight indicates a fineness converted for a fiber of 10,000 m in accordance with the method A of the fineness based on corrected weight in the test method of chemical fiber staple of JIS L1015.

EXAMPLE 2

A splittable conjugated fiber was produced according to the same conditions as in Example 1 except that crimping was not carried out and that the fiber length was 5 mm.

EXAMPLE 3

A splittable conjugated fiber was produced according to the same conditions as in Example 1 except that the PP/PE ratio was 30/70, the thickness of the non-oriented fiber was 27.5 dtex, and the fiber had a fineness based on corrected weight of 5.5 dtex, a fiber length of 64 mm, and 11 crimps per 25 mm.

EXAMPLE 4

A splittable conjugated fiber was produced according to the same conditions as in Example 1 except that the raw material polypropylene resin was PP2 in Table 1, the thickness of the non-oriented fiber was 55 dtex, and the fiber had a fineness based on corrected weight of 11 dtex, a fiber length of 76 mm, and 10 crimps per 25 mm.

EXAMPLE 5

A splittable conjugated fiber was produced according to the same conditions as in Example 1 except that the raw material polypropylene resin was PP3 in Table 1, the raw material polyethylene resin was PE2 in Table 1, the thickness of the non-oriented fiber was 27.5 dtex, and the fiber had a fineness based on corrected weight of 5.5 dtex, a fiber length of 64 mm, and 11 crimps per 25 mm.

EXAMPLE 6

Figure 6:
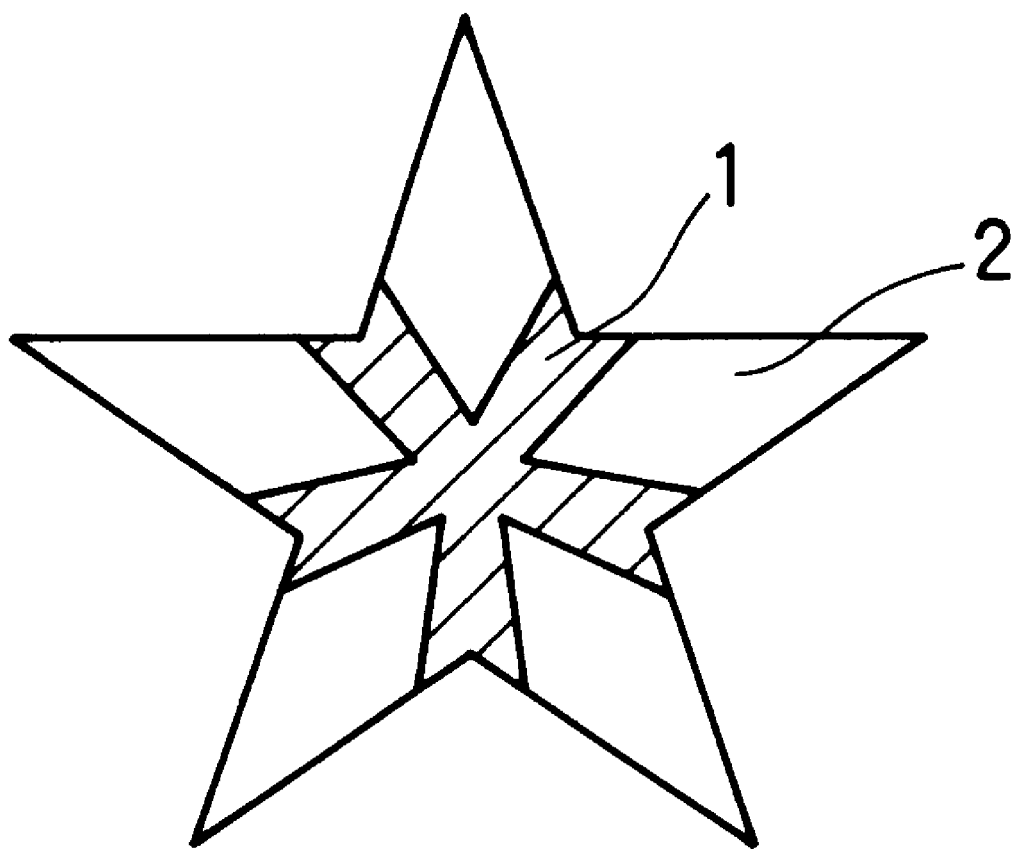
FIG. 6 is a cross-sectional view of a splittable conjugated fiber having a modified cross section (non-circular cross section) of the present invention.

A splittable conjugated fiber was produced according to the same conditions as in Example 1 except that the raw material polyethylene resin was PE2 in Table 1, the PP/PE ratio was 70/30, and the cross-sectional shape was as shown in FIG. 6. Moreover, polypropylene was used in the portion indicated by numeral 1 in FIG. 6, and polyethylene was used in the portion indicated by numeral 2 in FIG. 6.

EXAMPLE 7

A splittable conjugated fiber was produced according to the same conditions as in Example 1 except that the raw material polypropylene resin was PP4 in Table 1, and the raw material polyethylene resin was PE3 (containing a peroxide) in Table 1.

EXAMPLE 8

A splittable conjugated fiber was produced according to the same conditions as in Example 1 except that the raw material polyethylene resin was PE3 (containing a peroxide) in Table 1, the thickness of the non-oriented fiber was 27.5 dtex, and the fiber had a fineness based on corrected weight of 5.5 dtex, a fiber length of 64 mm, and 12 crimps per 25 mm.

EXAMPLE 9

The splittable conjugated fiber was produced according to the same conditions as in Example 1 except the conditions as follows:
Propylene/butene-1/ethylene terpolymer (95 wt. % of propylene component, 3 wt. % of butene-1 component, and 2 wt. % of ethylene component) [hereinafter abbreviated as PP5] was used in place of the raw material polypropylene resin, and ethylene/propylene copolymer (97 wt. % of ethylene component and 3 wt. % of propylene component) [hereinafter abbreviated as PE4] was used in place of the raw material polyethylene resin. Moreover, 2,5-dimethyl-2,5-di (tertiarybutylperoxy)hexane was used as the peroxide, and 0.01 wt. % of the peroxide was added to each of the components of PP5 and PE4. The PP5/PE4 ratio was 50/50, and the splittable conjugated fiber had properties as shown in Table 2.

Comparative Example 1

A splittable conjugated fiber was produced according to the same conditions as in Example 1 except that the raw material polypropylene resin was PP4 in Table 1.

Comparative Example 2

A splittable conjugated fiber was produced according to the same conditions as in Example 1 except that the raw material polypropylene resin was PP2 in Table 1, the raw material polyethylene resin was PE2 in Table 1, the thickness of the non-oriented fiber was 27.5 dtex, and the fiber had a fineness based on corrected weight of 5.5 dtex, a fiber length of 64 mm, and 11 crimps per 25 mm.

EXAMPLE 10

Using the fiber produced in Example 1, a web was obtained by roller carding. Then, the obtained web was processed by water jet, and the fiber was split off with a high-pressure water stream and at the same time entangled. Then, it was subjected to drying, so that a nonwoven fabric was produced.

Moreover, the water-jet process of the web was carried out as follows: The web obtained by roller carding was placed on a belt conveyor with a belt comprising a plain weave of 80 mesh, and a high-pressure water stream was injected from a nozzle plate in which many nozzles with a nozzle diameter of 0.1 mm were provided at a pitch between the nozzles of 1 mm. First, as in the condition 1 in Table 3, the web was preliminarily treated with a water pressure at 2MPa (the first stage), and then treated by splitting with a high water pressure at 4 MPa three times (the second through the fourth stages). Then, the entangled web was reversed, and under the same conditions as the above, and using the same nozzle plate, it was subjected to preliminary treatment and splitting with a high-pressure water stream, so that the conjugated fiber was split off and at the same time entangled.

Table 4 shows the basis weight, split ratio, rupture strength, and strength at 10% extension of the obtained nonwoven fabric. Moreover, the speed shown in Table 3 indicates the speed of moving the belt of the above-mentioned belt conveyor.

EXAMPLE 11

A nonwoven fabric was produced according to the same conditions as in Example 10 except that the fiber used was produced in Example 3.

EXAMPLE 12

A nonwoven fabric was produced according to the same conditions as in Example 10 except that the fiber used was produced in Example 4.

EXAMPLE 13

A nonwoven fabric was produced according to the same conditions as in Example 10 except that the fiber used was produced in Example 6.

EXAMPLE 14

A nonwoven fabric was produced according to the same conditions as in Example 10 except that the fiber used was produced in Example 7.

EXAMPLE 15

A nonwoven fabric was produced according to the same conditions as in Example 10 except that the fiber used was produced in EXAMPLE 8.

EXAMPLE 16

A nonwoven fabric was produced according to the same conditions as in Example 10 except that the fiber used was produced in Example 9.

Comparative Example 3

A nonwoven fabric was produced according to the same conditions as in Example 10 except that the fiber used was produced in Comparative Example 2 and the water jet process was carried out under the condition 2 in Table 3.

Comparative Example 4

A nonwoven fabric was produced according to the same conditions as in Example 10 except that the fiber used was produced in Comparative Example 1 and the water jet process was carried out under the condition 2 in Table 3.

EXAMPLE 17

A nonwoven fabric was produced according to the same method as in Example 10 except that 30 wt. % of rayon fiber (produced by Kohjin Co., Ltd.) having a thickness of 1.6 dtex and a length of 45 mm was blended with 70 wt. % of the splittable conjugated fiber produced in Example 1. The nonwoven fabric had a basis weight of 38 g/m², a split ratio of 91%, and a rupture strength of 132 N/5 cm in MD and 18 N/5 cm in CD. The nonwoven fabric also had a strength at 10% extension of 70 N/5 cm in MD and 0.8 N/5 cm in CD. The formation of the nonwoven fabric was evaluated as ○.

EXAMPLE 18

Using the fiber without crimps as produced in Example 2, and using an angular sheeting machine (25 cm square), a nonwoven fabric was obtained by the wet process. 26 g of a fiber with a moisture content of 30 wt. % was stirred in 1 dm³ of tap water for five minutes by a beater. Then, 125 cm³ of the fiber-dispersed water, which was dispersed uniformly, was dispersed in about 15 dm³ of tap water uniformly in a vessel of an angular sheeting machine. Then, the dispersion was filtered with a metallic mesh filter, and its moisture was wiped off with a filter paper, so that only the fiber was collected. After drying at 105° C. for 3 minutes with a "Yankee dryer" manufactured by Kumagai Rikikogyo Co., Ltd., it was heat treated at 135° C., for 12 seconds by a through-air machine, so that a nonwoven fabric in which the polyethylene resin in the fiber was melt-bonded was obtained. The wet-processed nonwoven fabric thus obtained had a basis weight of 41 g/m², a split ratio of 86%, and a rupture strength of 75 N/5 cm in MD and 72 N/5 cm in CD. The formation of the nonwoven fabric was evaluated as ○.

EXAMPLE 19

Using a commercial disposable diaper having an approximately I-shape in a flat surface ("Elleair Friend: for new-born infant" produced by Daio Paper Corporation), only its top surface material was substantially replaced by the nonwoven fabric blended with rayon as mentioned in Example 17.

In this commercial disposable diaper, staple fiber of polyethylene/polypropylene-based thermal melt-bonding conjugated fiber (core/sheath type conjugated fiber) was used, and a nonwoven fabric in which fibers are thermally melt-bonded at the points of intersection was used as a top surface material, pulp and high water-absorbent resin were used as the main components of a water-absorbent material, and a polyethylene film was used as a back surface material. Only the top surface material was removed from the diaper by cutting with a knife. The rayon-blended nonwoven fabric obtained in Example 17 was laminated in the place of the top surface material, which was cut and removed. Furthermore, the nonwoven fabric having a thermally bonding property as obtained in Example 17 was thermally melt-bonded with the remainder of the nonwoven fabric in the vicinities of the leg parts. Thus, a disposable diaper in which the nonwoven fabric obtained in Example 17 was placed as its top surface material was obtained. The top surface material of this diaper had a very soft feeling, and it was suitable as a disposable diaper for a new-born infant who has especially delicate skin.

TABLE 1

Resin Used

| Type | Peroxide | Added Amount (wt. %) | Resin MFR (g/10 min) |
|---|---|---|---|
| PP1 | 2,5-dimethyl-2,5-di(tertiarybutylperoxy)hexane | 0.02 | 36 |
| PP2 | 1,3-bis(tertiarybutylperoxyisopropyl)benzene | 0.01 | 8 |
| PP3 | ditertiarybutylhydroperoxide | 0.01 | 32 |
| PP4 | none | 0 | 23 |
| PP5 | 2,5-dimethyl-2,5-di(tertiarybutylperoxy)hexane | 0.01 | 28 |
| PE1 | none | 0 | 41 |
| PE2 | none | 0 | 26 |
| PE3 | 2,5-dimethyl-2,5-di(tertiarybutylperoxy)hexane | 0.01 | 27 |
| PE4 | 2,5-dimethyl-2,5-di(tertiarybutylperoxy)hexane | 0.01 | 18 |

TABLE 2

Properties of Fiber

| Example | Fineness based on corrected weight (dtex) | Cut Length (mm) | PP/PE Ratio | Fiber MFR (g/10 min) |
|---|---|---|---|---|
| Example 1 | 1.6 | 45 | PP1/PE1 = 50/50 | 46 |
| Example 2 | 1.6 | 5 | PP1/PE1 = 50/50 | 46 |
| Example 3 | 5.5 | 64 | PP1/PE1 = 30/70 | 44 |
| Example 4 | 11 | 76 | PP2/PE1 = 50/50 | 34 |
| Example 5 | 5.5 | 64 | PP3/PE2 = 50/50 | 37 |
| Example 6 | 1.6 | 45 | PP1/PE2 = 70/30 | 44 |
| Example 7 | 1.6 | 45 | PP4/PE3 = 50/50 | 48 |
| Example 8 | 5.5 | 64 | PP1/PE3 = 50/50 | 48 |
| Example 9 | 1.6 | 45 | PP5/PE4 = 50/50 | 33 |
| Compar. Ex. 1 | 1.6 | 45 | PP4/PE1 = 50/50 | 40 |
| Compar. Ex. 2 | 5.5 | 64 | PP2/PE2 = 50/50 | 28 |

| Example | Rupture Strength (cN/dtex) | Rupture Elongation (%) | Number of Crimps (Crimps/25mm) | Cross-Sectional Shape | Spinnability | Stretchability |
|---|---|---|---|---|---|---|
| Example 1 | 3.5 | 45 | 13 | FIG. 3 | ○ | ○ |
| Example 2 | 3.7 | 48 | none | FIG. 3 | ○ | ○ |
| Example 3 | 2.9 | 53 | 11 | FIG. 3 | ○ | ○ |
| Example 4 | 2.7 | 59 | 10 | FIG. 3 | ○ | ○ |
| Example 5 | 3.1 | 55 | 11 | FIG. 3 | ○ | ○ |
| Example 6 | 3.7 | 43 | 13 | FIG. 6 | ○ | ○ |
| Example 7 | 3.6 | 43 | 12 | FIG. 3 | ○ | ○ |
| Example 8 | 3.4 | 47 | 12 | FIG. 3 | ○ | ○ |
| Example 9 | 2.8 | 45 | 12 | FIG. 3 | ○ | ○ |
| Compar. Ex. 1 | 2.9 | 50 | 13 | FIG. 3 | Δ | Δ |
| Compar. Ex. 2 | 2.7 | 57 | 11 | FIG. 3 | Δ | Δ |

TABLE 3

Conditions of Operating a Water-Jet Processing Apparatus

| | Pressure (MPa) | | | | |
|---|---|---|---|---|---|
| | First Stage | Second Stage | Third Stage | Fourth Stage | Speed (m/min) |
| Condition 1 | 2 | 4 | 4 | 4 | 60 |
| Condition 2 | 2 | 8 | 8 | 8 | 60 |

TABLE 4

Properties of Nonwoven Fabric

| Example | Fiber | Basis Weight (g/m²) | Split Ratio (%) | WJ Condition | Strength of Nonwoven Fabric (N/5 cm) | | | | Formation of Nonwoven Fabric |
|---|---|---|---|---|---|---|---|---|---|
| | | | | | Rupture | | At 10% Extension | | |
| | | | | | MD | CD | MD | CD | |
| Example 10 | Example 1 | 41 | 93 | Condition 1 | 156 | 23 | 76 | 1.1 | ○ |
| Example 11 | Example 3 | 41 | 90 | Condition 1 | 126 | 18 | 65 | 0.9 | ○ |
| Example 12 | Example 4 | 42 | 87 | Condition 1 | 70 | 11 | 37 | 0.5 | ○ |
| Example 13 | Example 6 | 41 | 92 | Condition 1 | 96 | 14 | 46 | 0.7 | ○ |
| Example 14 | Example 7 | 40 | 82 | Condition 1 | 150 | 22 | 73 | 1.1 | Δ |
| Example 15 | Example 8 | 38 | 92 | Condition 1 | 132 | 21 | 68 | 1.0 | ○ |
| Example 16 | Example 9 | 39 | 85 | Condition 1 | 128 | 19 | 70 | 1.0 | ○ |
| Compar. Ex. 3 | Compar. Ex. 2 | 42 | 54 | Condition 2 | 70 | 11 | 37 | 0.5 | X |
| Compar. Ex. 4 | Compar. Ex. 1 | 41 | 62 | Condition 2 | 61 | 9 | 31 | 0.4 | X |

As is evident from the results of Table 4, when the fiber MFR was at least 30 g/10 min, and a peroxide was contained in the polyolefin resin, the splittable conjugated fiber in a nonwoven fabric had an increased split ratio.

That is, the splittable conjugated fiber became easy to split, and a soft nonwoven fabric was obtained without impairing good formation of the nonwoven fabric.

By solving difficulty in splitting, which has been a conventional problem for a polyolefin-based splittable conjugated fiber, a nonwoven fabric that is soft and uniform and has a good formation can be produced using the splittable conjugated fiber of the present invention.

Thus, a drawback in practice, which has been a conventional problem for a nonwoven fabric obtained by splitting a splittable conjugated fiber, that because of the large impact required for the splitting, non-uniformity is generated in the obtained nonwoven fabric, and only a nonwoven fabric with poor formation can be obtained, can be solved.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A polyolefin-based splittable conjugated fiber that contains a peroxide and has a melt flow rate of at least 30 g/10 min, wherein the content of the peroxide is from 0.005 to 0.3 wt. % based on the total weight of the polyolefin-based splittable conjugated fiber.

2. The polyolefin-based splittable conjugated fiber according to claim 1, which comprises a polypropylene resin and a polyethylene resin.

3. The polyolefin-based splittable conjugated fiber according to claim 1, wherein the peroxide is dialkylperoxide.

4. The polyolefin-based splittable conjugated fiber according to claim 1, which has a modified cross section.

5. A nonwoven fabric, comprising split fibers obtained by splitting the splittable conjugated fiber according to claim 1.

6. An absorbent article using the nonwoven fabric according to claim 5 in a part thereof.

* * * * *